United States Patent
Andrews et al.

(10) Patent No.: US 6,769,306 B2
(45) Date of Patent: Aug. 3, 2004

(54) LOG CUTTING PROCEDURES

(75) Inventors: Michael Kenneth Andrews, Wellington (NZ); Paul David Harris, Wellington (NZ); Peter Charles Stratton Carter, Rotorua (NZ); Brian Andrew Rawley, Tokoroa (NZ); Marcus Jean Francois Lausberg, Rotorua (NZ)

(73) Assignee: Carter Holt Harvey Limited, Manukau (NZ)

( * ) Notice: Subject to any disclaimer, the term of this patent is extended or adjusted under 35 U.S.C. 154(b) by 0 days.

(21) Appl. No.: 10/361,015

(22) Filed: Feb. 10, 2003

(65) Prior Publication Data

US 2003/0216829 A1 Nov. 20, 2003

Related U.S. Application Data

(63) Continuation of application No. 09/857,173, filed as application No. PCT/NZ99/00134 on Aug. 17, 1999, now abandoned.

(30) Foreign Application Priority Data

Dec. 17, 1998 (NZ) ................................................ 333434

(51) Int. Cl.$^7$ .............................................. G01N 29/18
(52) U.S. Cl. .......................................... 73/597; 73/602
(58) Field of Search .......................... 73/597, 602, 622, 73/73, 75, 432.1; 702/38–40, 35, 81, 189, 179–181, 196, 126, 134–136, 155

(56) References Cited

U.S. PATENT DOCUMENTS

| | | | |
|---|---|---|---|
| 4,702,111 A | * | 10/1987 | Holland ........................ 73/579 |
| 4,852,029 A | * | 7/1989 | Pope et al. .................... 702/41 |
| 4,858,469 A | * | 8/1989 | Hosgood et al. ............... 73/579 |
| 4,899,588 A | * | 2/1990 | Titlow et al. .................. 73/597 |
| 5,024,091 A | * | 6/1991 | Pellerin et al. ............... 73/597 |
| 5,097,881 A | * | 3/1992 | Mack ........................... 144/356 |
| 5,224,381 A | * | 7/1993 | Sandoz et al. ................ 73/597 |
| 5,396,799 A | * | 3/1995 | Ross et al. .................... 73/579 |
| 5,983,701 A | * | 11/1999 | Hassani et al. ............ 73/12.01 |
| 6,305,224 B1 | * | 10/2001 | Stanish et al. ................ 73/597 |

FOREIGN PATENT DOCUMENTS

| | | |
|---|---|---|
| DE | 4435975 | 4/1995 |
| GB | 1244699 | 9/1971 |
| WO | WO98/01737 | 1/1998 |

OTHER PUBLICATIONS

Patent Abstracts of Japan, JP 07–103945 A (Aratake et al) Apr. 21, 1995.
Derwent Abstract Accession No. 97–523076/48, JP 9–251006A (Shizuoka Seiki Co Ltd), Sep. 22, 1997.
Patent Abstracts of Japan, JP 6–018388A (Ichijiyou Komuten: KK) Jan. 25, 1994.
Derwent Abstract Accession No. 0–311634/41, SU 1530986A (EGIN), Dec. 23, 1989.

\* cited by examiner

*Primary Examiner*—Hezron Williams
*Assistant Examiner*—Rose M. Miller
(74) *Attorney, Agent, or Firm*—Jacobson Holman PLLC

(57) ABSTRACT

Use of a single end testing of stems of felled trees whereby by inducing a sonic wave with an impact and by reference to detected reflections and with a knowledge of the length of the stem the stiffness and/or strength characteristics of the stem or logs to be cut therefrom can be derived. A preferred procedure is a determination of the fundamental frequency $f_0$ which relates to velocity V, the speed of longitudinal compressional motions along the stem, and L, the length of the stem, as follows: $V = 2Lf_0$. From that value V or a function of V can be derived an indicator of stiffness and/or strength.

7 Claims, 4 Drawing Sheets

LOG CUTTING PROCEDURES

This is a Continuation of application Ser. No. 09/857,173 filed Sep. 27, 2001, now abandoned, which in turn is a nationalization of PCT/NZ99/00134 filed Aug. 17, 1999.

FIELD OF THE INVENTION

The present invention relates to a method of deriving a (surrogate) measure of stiffness and/or strength of sections of the stem of a felled tree (e.g., so as to be determinative of possible destinies of logs to be cut from the stem), a method of log making or log use determination for logs made or to be made from a felled tree with a view to maximizing stiffness and/or strength related extracted value therefrom, procedures involved in such methods and to related apparatus and means.

The invention also relates to the apparatus useful in such a procedure and to its use.

BACKGROUND OF THE INVENTION

The timber industry faces a need to efficiently utilise its rather variable forest resource. Timber classification, for example machine stress grading, is currently done at the end of the production chain. This process results in wastage from processing which ultimately proves to have been inappropriate. Clearly, it would be more efficient to measure log properties early in the chain and process the logs accordingly.

As recognised in British Patent 1244699 of Washington State University Research Foundation (the full content of which is hereby included by way of reference) non-destructive individual valuation of wood products is often desirable because of the inherent variability of wood as a material particularly where a wooden member is to be used for a purpose that requires knowledge of its ability to perform to a minimum structural standard.

The aforementioned patent contemplates, in addition to visual inspection, a non-destructive method of grading logs by a procedure where properties are determined along a selected length of a specimen by means of longitudinal energy wave propagation through the selected length thereof. This was achieved by locating a first sensor in proximity to a surface of the specimen at one end of the selected length thereof and locating a second sensor in proximity to a surface of the specimen at the remaining end of the selected length thereof, impacting one end of the specimen itself to set up an energy wave within the specimen to travel in a longitudinal direction to encounter and then move along the selected length of the specimen between the sensors measuring the time of passage of the energy wave between the sensors and determining mechanical properties of the specimen as related to the measured time of passage of the energy wave through the selected length.

A dynamic modulus of elasticity (hereinafter MOE) was derived by the product of (a) the square of the velocity of wave propagation (i.e., length of the selected specimen length divided by the time of passage of wave)(i.e., $V^2$) and (b) the specimen density($\rho$).

Such procedures disclosed in British Patent 1244699 are not of a kind usable in a forest with a minimum of labour in the time frame usually required for marking up a felled tree which is to then be broken into logs by appropriately positioned cuts.

It is of course possible to assign different destinies to different logs to be cut from the same stem of a felled tree which will maximize the extracted value of the harvesting of the particular tree. This has been recognised in New Zealand and elsewhere by software packages such as those of the New Zealand Forest Research Institute (i.e., the AVIS™ Software) or previously used by LIRO (i.e., the New Zealand Logging Industry Research Organisation).

A device of favour in the log forming industry in New Zealand is of a kind typified by that disclosed in U.S. Pat. No. 5,457,635 of Interpine Export (NZ) Limited (the full content of which is hereby included by way of reference).

U.S. Pat. No. 5,457,635 discloses apparatus for determining cut positions in stems of felled trees. The apparatus has distance measuring means which provide an output signal representative of length for determining lengths along the stem. The apparatus also has diameter measuring means which provides an output signal representative of diameter for determining the diameter of a stem at selected positions along the stem. Data entry means are adapted to receive and output selected information relating to the quality of a stem at various positions along the stem. Computing means are also provided on the apparatus which (in response to input signals from the distance measuring means, diameter measuring means and data entry means) determines the preferred cutting positions on the stem to optimize the millable timber obtained from the stem. Output means allow information determined by the computer means to be presented to the user so that the stem may then be appropriately marked with cut positions.

Such a product however does not provide an indication of a preferred destiny for individual logs to be cut from the stem reliant in any way upon any actual or surrogate measure of stiffness and/or strength. Stiffness and/or strength (whether MOE or a surrogate measure thereof) is a characteristic of the structural quality of the wood in the logs and is fundamental to its performance in certain uses.

The computer software referred to in U.S. Pat. No. 5,457,635 consists of an optimizing algorithm which works in conjunction with a log type file or library. The log type file or library contains specifications for each log type to be considered along with a relative value representing the desirability of each log type. This software is presented with the input of measurements of length, diameter and curvature of the stem. There is also provision for the manual inputting of the number and size of knots (as a quality code).

The input information then allows the algorithm to "fit" the best value combination of logs to be cut from the stem thus providing an optimum solution in terms of the value returned by the stem when cut into logs.

SUMMARY OF THE INVENTION

The present invention recognises that the MOE is a good indicator of the structural characteristics of timber. The MOE is related to the speed V of a longitudinal compression wave by the relation $$MOE = \rho V^2$$

where $\rho$ is the density of the wooden material. In dried wood (about 12% moisture content) it is known that the modulus correlates approximately with the density $\rho$. In a freshly cut stem or log, the density in large measure is due to the free water content, and the value is in the vicinity of 1000 kg/m$^3$. The modulus is determined by the indicator $V^2$ by measurement (preferably at low frequency as hereinafter described) of the velocity V. Indeed the present invention recognises the value of a measure of V or a function of V owing to its 2nd order use in the MOE formula above.

Apparatus such as the PILODYN™ (density penetrometer which estimates only outer wood density) procedure as a measure of wood characteristics is therefore far less attractive as an indicator of wood performance for structural or other purposes than is the longitudinal wave propagation V or function of V (e.g., elapsed time values) procedure hereinafter described to interpolate to logs along the stem length a surrogate stiffness and/or strength (and thus stiffness and/or strength related value enhancing destiny).

The present invention also recognises the value of the simple relationship where V can be determined by determining (particularly at low frequency) an equivalent fundamental resonance frequency ($f_0$) using the relationship V×resonant frequency×twice the length ($L$) of the stem.

The present invention therefore in a first aspect consists in a method of log making (or at least cut positioning for log making) from the stem of a felled tree with a view to maximizing stiffness and/or strength related extracted value therefrom, which method includes inducing from an end of the stem of the felled tree a sonic wave (as hereinafter described) to travel along the length of the stem of the felled tree, reflecting repeatedly at the free ends, deriving by reference to the tree stem length (or multiples thereof) and the appropriate resonant frequency for the stem V or $V^2$ or a function of V or $V^2$, and then using that output of V or $V^2$ or a function of V or $V^2$
(i) as a factor in determining cut positions for a number of logs from the tested felled tree stem, and
(ii) as a prime factor in determining end use for each or at least some of the logs.

Preferably for the purpose of steps (i) and/or (ii) there is reference to a library of known stiffness and/or strength characteristics [whether MOE, $V^2$, V, elapsed time, resonant frequency or some other surrogate value] in relation to known sonic wave travel values typical or generic of trees of the felled tree condition.

Preferably the deriving of the function of V or $V^2$ value comprises the steps of at one end of the stem of a felled tree (preferably after the removal of all branches), inducing an energy input (e.g., by striking or otherwise) and detecting at that same end the resonant frequencies using spectral analysis of the sequence of multiply reflected returns of the input energy and deriving from the spectrum by appropriate calculations a value of V or a function of V by reference to the known length of the stem.

For the purpose of such detection any suitable apparatus may be used by way of example see U.S. Pat. No. 5,396,799 of Ross et al. U.S. Pat. No. 5,396,799 deals with the measurement of an induced acoustic wave past a detector between the ends of a ground supported vertical pole.

U.S. Pat. No. 5,396,799 discloses the use of impacting means to induce the sonic or acoustic wave and a detection of the passage of the wave past a laterally positioned piezo electric transducer based detector. Those or alternative forms of detection and/or wave propagation can be utilised by the present invention.

The present invention however envisages detection at the same end from which the impact is induced so as to minimise the complexity of the process. The function of V then becomes a manual or automatic input to computing means as will hereinafter be described. Such computing means may, for example, be a derivative of the form of apparatus described in the aforementioned U.S. Pat. No. 5,457,635.

The present invention in a further aspect consists in a method of determining a value indicative of stiffness and/or strength or useful for that purpose (e.g., V or a function of V) [which may optionally be squared to provide a better surrogate value of stiffness and/or strength] which comprises inducing into one end of the stem of a felled tree an acoustical input (e.g., by striking or other means) and by detecting subsequent reflected sound therefrom or otherwise using that input to provide a measure of resonant frequencies and by reference to the length of the stem, determining a value indicative of V or $V^2$ or a function or V or $V^2$ (e.g.; MOE) by reliance on the resonant frequencies.

In still a further aspect the present invention consists in a method of log making or log use determination for logs made or to be made from a felled tree with a view to maximizing stiffness and/or strength related extracted value therefrom, said method comprising (i) determining
   (a) at least one or more of
       stem diameter,
       stem sweep,
       branch size,
       internodal length,
       stem length, and
       feasible log length,
   (b) a surrogate measure of stiffness and/or strength for the stem derived from the resonant frequency of an induced sound wave along at least the full stem (ii) by computer or machine reference to a library of known stiffness and/or strength characteristics in relation to known values of the same type surrogate measure of stiffness and/or strength (or a squaring thereof) typical or generic of trees of the felled tree condition and determining value attributed to different stiffness and/or strength characteristics and/or deriving potential cut positions for discrete logs which take account of stiffness and/or strength related values, such cutting positions determining a preferred destiny or range of destinies.

The log making optimisations may be those disclosed in Interpine Export (NZ) Limited U.S. Pat. No. 5,457,635, the full content of which is here introduced by way of reference.

As used herein all reference to the term "sonic wave" is to be considered synonymous with any energy wave of a vibrational kind that may be induced along the length of the stem of a tree (which might variously be referred to as an induced stress wave, an induced energy wave, an induced acoustic wave, etc).

As used herein reference to deriving or determining a value includes any algorithm into which values are entered and from which V, $V^2$ or a function of V or $V^2$ can be derived whether the actual calculation need be made (e.g., a computer) prior to being used as a surrogate stiffness and/or strength value.

In a further aspect the present invention consists in a method of providing an indicator of or from which stiffness and/or strength can be estimated, which method involves an operative use of apparatus as hereinafter described or as disclosed in our New Zealand Patent Specification No. 337015 filed Jul. 30, 1999.

In still a further aspect the present invention consists in a method of providing an indicator of or from which stiffness and/or strength can be estimated for a felled log of known or measurable length L, said method comprising or including the steps of striking an end of the felled log whilst having sensing means in contact with the log end to detect one or both of (i) the impulse and at least one echo of the impulse resulting from the striking of that same log end and (ii) multiple echoes of the impulse resulting from the striking of that same log end, processing the output of at least said sensing means in processing means to derive, using an echo or echoes sensed by said sensing means, a said indicator, and displaying said indicator or any derivative thereof received from said processing means, optionally thereafter appropriately marking or otherwise indicating the fate of the log on the basis of the displayed indicator, said process being further characterised in that said processing means tests frequency transformed data derived from time based echo data with a view to deriving a measure or good estimate of fundamental frequency $f_0$, L has been, is or can be entered into said processing means, and said processing means derives said indicator by reference to both $f_0$ and L.

Preferably said indicator is an estimation of MOE for a green felled log on the basis of an estimation of $\rho=1000$ kg/m$^3$.

BRIEF DESCRIPTION OF THE DRAWINGS

Preferred forms of the present invention will now be described with reference to the accompanying drawings in which.

DETAILED DESCRIPTION OF THE PREFERRED EMBODIMENTS

Stiffness and/or strength measurement is a parameter which has had recent prominence, both in regard to log and timber stiffness and/or strength and the implications it has for the basic constituent fibres of the wood. Measurement of stiffness and/or strength using so-called stress wave timers, that is to say electronic instruments which detect the time of flight of a sonic impulse along or across a piece of wood have been in use for many years. While it is generally accepted that they measure a quantity indicative of mechanical stiffness and/or strength, for forest use, they tend to be of marginal accuracy, and relatively insensitive (due their inherent broadband nature) and therefore difficult or impossible to apply to long logs. Their fatal flaw is that they require double ended operation, i.e. detectors need to be placed at each end of the log under test. Logistically, this is unacceptable in forest use.

In 1986, Sobue demonstrated the excitation of longitudinal resonances from a log or beam which had been struck by a hammer, their detection by a single sensor, and their identification by Fourier analysis. However this process was well understood as a general analysis method in material analysis prior to that time. This development however demonstrated that single-ended testing of logs to obtain an indication of stiffness and/or strength modulus was possible. In general, subsequent developments have used commercial elements such as spectrum analysers, or standard computers, which mean that true field-portability has not been achieved and it has not been possible to survey production quantities of timber.

Figure 3:
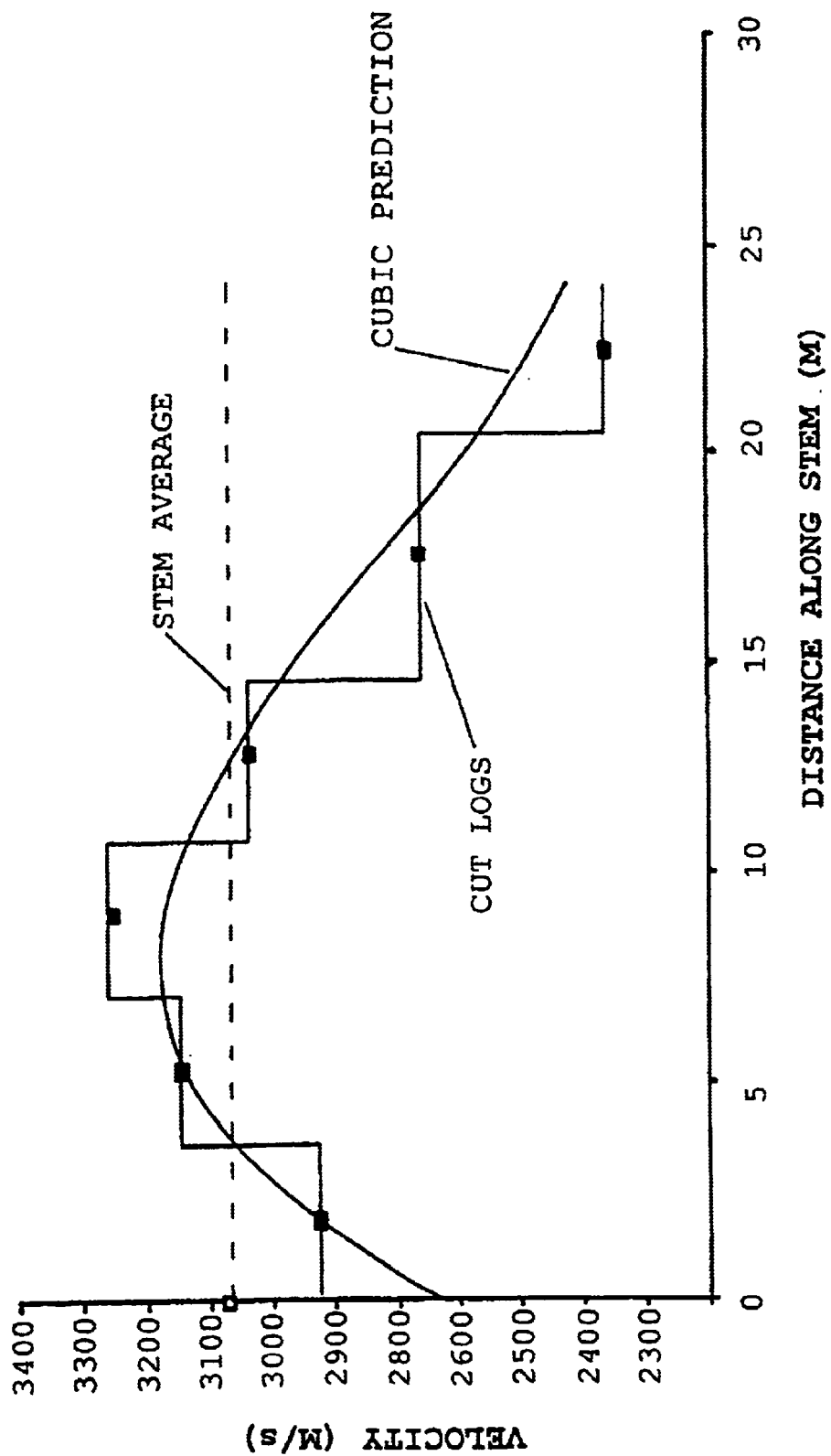
FIG. 3 illustrates how whole stem velocity information, combined with a knowledge of typical velocity profiles along a steam, can predict velocities within logs subsequently cut from the stem.

In FIG. 3, the constant term in the cubic has been adjusted by calculation so that the transit time derived by integrating the speeds from the cubic expression along a particular stem equals the time found from the averaged velocity V along the stem. The curve drawn is the resulting prediction of speed along that stem. Also shown in FIG. 3 as the stepped line are speeds subsequently measured in the sequence of logs made from that stem. Clearly in this example, a combination of reference information and stem-average measurement has enabled a considerable improvement to be made in velocity or stiffness and/or strength estimation along the stem prior to making cuts.

Measurements carried out by us on wood as it is dried from the green to dry state have shown that there is good agreement between the static bending modulus and the so-called dynamic MOE found from the formula $$MOE = \rho V^2$$

where V is the velocity of longitudinal waves along the log or beam and $\rho$ is the mass density of the wood, including its water content. This agreement is possibly because the effective measurement frequency is low (hundreds of Hz) rather than in the ultrasonic range often reported in the literature. Ultrasonic measurements show a water-dependent modulus. The low frequency agreement has profound significance for the log or timber industry; since the density of green wood is known to be about 1000 kg/m$^1$, regardless of the dry density. The modulus can therefore be estimated from a green velocity measurement alone. The dry value can be estimated as being perhaps 15% above this as the wood cellulose dries from saturation to equilibrium water content.

The present invention in its preferred form recognises that accurate measurement of the sonic velocity of logs or stems can be made in a time of a second from the identification of impact-induced resonances found by Fourier analysis and a good estimate of the stiffness and/or strength modulus found. The three elements of apparatus required are the measuring head, the signal acquisition and processing hardware 4, and the algorithms 5 needed to interpret the resonance data.

Figure 1:
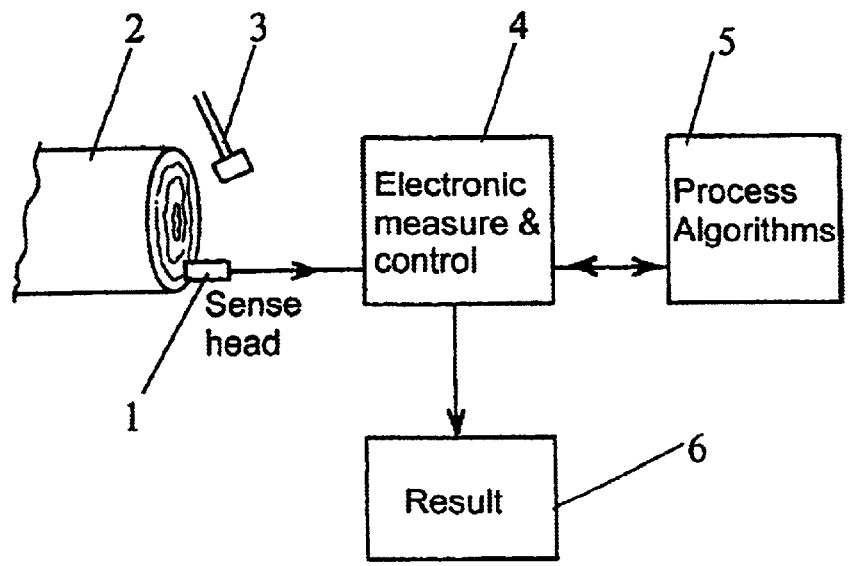
FIG. 1 shows an MOE measuring instrument including an accelerometer sense head 1 as it is preferably used against a log end 2 in conjunction with a hammer 3 and data interpretation devices to yield a result 6 such as a result to be used.

In this respect see FIG. 1.

General Instrument Requirements

The requirements for a portable, hand-held tool for log assessment, able to be used by a single operator in a yard or forest are Low weight and small size Ease of operation in obtaining the measurement Fast processing and display of answer, e.g. second.

Low battery drain, e.g. operation for at least one shift on a battery

Rugged construction with a degree of waterproofing.

Robust processing algorithms able to handle variable quality data

Low cost if many units are to be deployed by technically unskilled operators

Some of these requirements are potentially contradictory, such as ruggedized but lightweight construction, fast processing but small current drain. In particular, though small "laptop" style computers are available, it is unlikely that waterproofing, full shift operation and low cost can be easily achieved. It is generally more efficient to use dedicated hardware which incorporates the analogue signal acquisition, its digitisation and processing into a characteristic spectrum, further software algorithms to interpret the data, and a small, low power display rather than the full screen of a computer. Such a configuration allows major savings of power, as will be described.

Sensing Head

Figure 5:
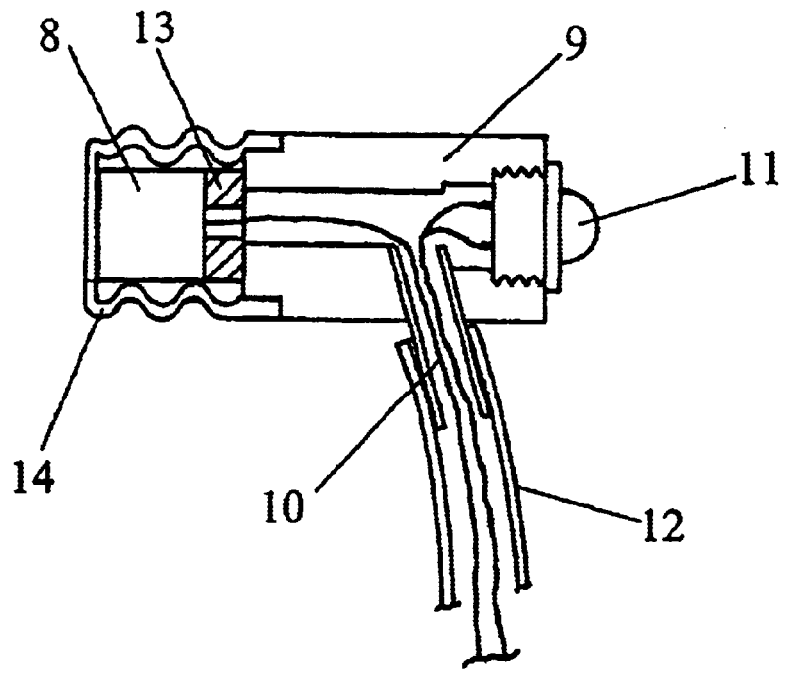
FIG. 5 shows a preferred sensing head.

FIG. 5 shows the sensing head, comprising a piezo-style accelerometer 8 mounted on a body 9 which contains a cable entry 10 for the wires to the accelerometer 8, and a switch 11. The wires are further protected mechanically by flexible tubing 12 which also prevents water ingress to the head and which extends to the electronic unit to be described. The frequency response of the accelerometer may be chosen for the nature of the log expected. For normal forest work, a frequency response of 10 to 3000 Hz is adequate, but wider ranges may be advantageously used, particularly if the instrument is to be used in research applications. It is preferable that the accelerometer incorporates a charge amplifier, since connection to the electronic unit may then be made through a cable of any length. The purpose of the switch 11 is to activate the signal acquisition circuits immediately prior to striking the log under test. It is desirable that the accelerometer is compliantly mounted on the body, for example on a pad of silicone rubber 13, as this enables the operator to press the head against the timber face and maintain good contact independently of any hand movement. If the accelerometer mount is rigid, spurious acceleration signals may be generated if the flat face of the accelerometer is inadvertently rocked against the timber. A thin cap 14 of material such as neoprene rubber is fixed over the end of the head so as to be in contact with the accelerometer end face. The purpose of this is to provide some protection for the accelerometer against inevitable build up of debris such as resin from the logs under test. The cap may be cleaned or replaced. Tests have shown that 1 mm of a hard rubber does not significantly impair collection of acoustic signals from logs.

To take a measurement, it is sufficient to press the assembly against the end face of the log, depress the switch 11 (an action designed to encourage pressure contact with the timber) and strike the timber cleanly but not forcefully with a mallet or hammer. Pressure contact must be maintained for up to half a second while the sound waves within the log decay.

Signals may be collected reliably with this head regardless of the nature of the cross-cut face; for example, the deep ridges produced by the hydraulic saws in automatic harvesters such as the WARRATAH™ generate signals no different from more even surfaces. It is not necessary to embed the detector in the wood to achieve coupling, a fact that considerably speeds up the sounding operation. Experience has shown that neither placement of the head or the blow is critical. This is understandable since the system analyses many tens of reflections of the acoustic pulse in modes which incorporate the entire log, so the precise nature of the initial shock becomes unimportant. This is in clear distinction from so-called stress wave testers, where a single transit time of an acoustic pulse is measured. Clearly, for stress wave testers, the initial development of the pulse from a hammer-generated, localised, near spherical disturbance, to a mode filling the log may be a significant fraction of the first transit. Nevertheless, good practice seems to be to place both the head and position the blow perhaps a quarter of the distance from the log centre to the bark. Peripheral blows tend to encourage non-longitudinal oscillations of the sample, which are not wanted.

Experience shows that unskilled operators have the unshakeable belief that if modest blows produce results, then Herculean strikes must be even more effective. This tendency can be controlled by issuing a hammer of appropriate weight for the task. For logs and stems, a weight of 400 gm is adequate. For lighter samples, such as sawn and dried framing timber, lighter mallets can be used. Only on very short logs of exceptionally large diameter have heavy hammers been beneficial in exciting clean resonances.

Electronic Unit

The two dominating considerations of this unit are the high rate of decay of the signal coming from the wood, and the need to reduce power consumption as much as possible so that effectively continuous operation on small batteries for at least one shift is possible. Consideration of currents drawn by processors capable of performing the functions required here show that some automatic form of power saving is necessary.

Figure 4:
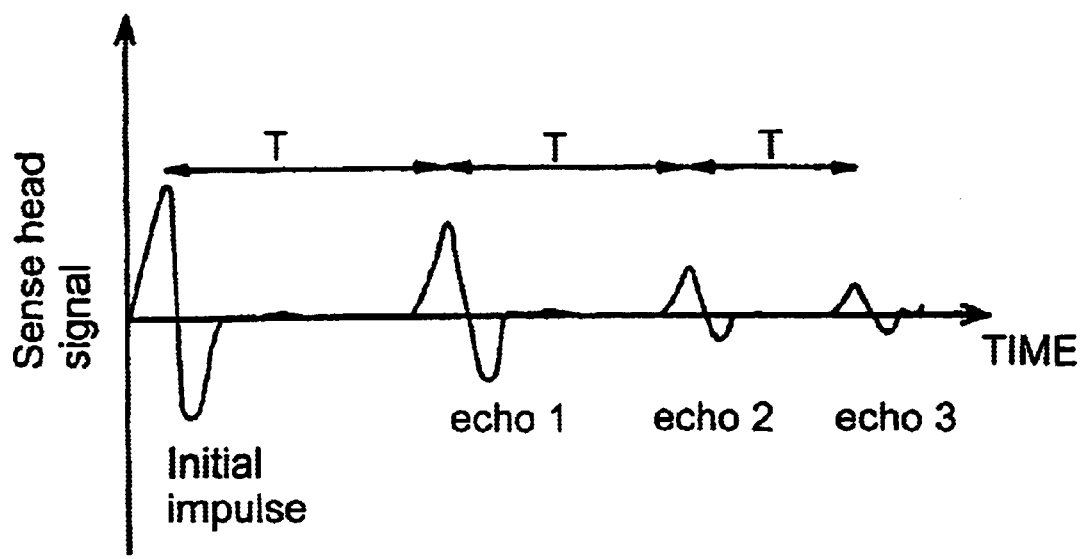
FIG. 4 shows echo decay.

Measurements of the attenuation of acoustic signals in wet wood show that the signal can fall by 60 dB in 0.1 s, in an approximately logarithmic fashion. The process of Fourier analysis in this application can be thought of as a simple way of averaging the echo times of many reflections, since the fundamental frequency ffound by Fourier analysis is the inverse of the inverse of the echo time T. (FIG. 4) The reception of many echos leads to an accurate average. It is for this reason that resonance-type instruments produce more consistent answers than single transit stress-wave timers. However the echo time in a long stem is typically 10 ms. To detect 20 echos necessitates detecting signal for 200 ms, and clearly by this time the amplitude will be very low if the attenuation is 60 dB/100 ms.

To obtain useful signals for a duration of 0.1 to 0.4 s, the gain of the analogue amplifier is made to increase at a constant logarithmic rate, for example 20 to 60 dB, over the course of the event to partially offset the natural attenuation. Amplifier offset voltages must be carefully controlled with such a strategy to prevent dc contamination of the final spectrum. In conjunction with this, high resolution A/D converters, typically 14 bit, are used so that useful resolution can still be obtained where the signal has fallen into the microvolt range (but is still above the noise background). If the initial acoustic signal is converted to a 3V amplitude signal, the level 100 ms after this might be 3 mV, which would give some resolution on a 14 bit converter set to 3V scale, since the least significant bit is 0.19 mvolt. However, signals beyond the 100 ms time frame would quickly fail to be digitized.

The provision of time-dependent gain extends the period over which signals can be usefully digitised. 20 dB of gain over the 100 ms described above would raise the signal at that time to 30 mv, enabling useful digitization to be considerably extended.

Figure 6:
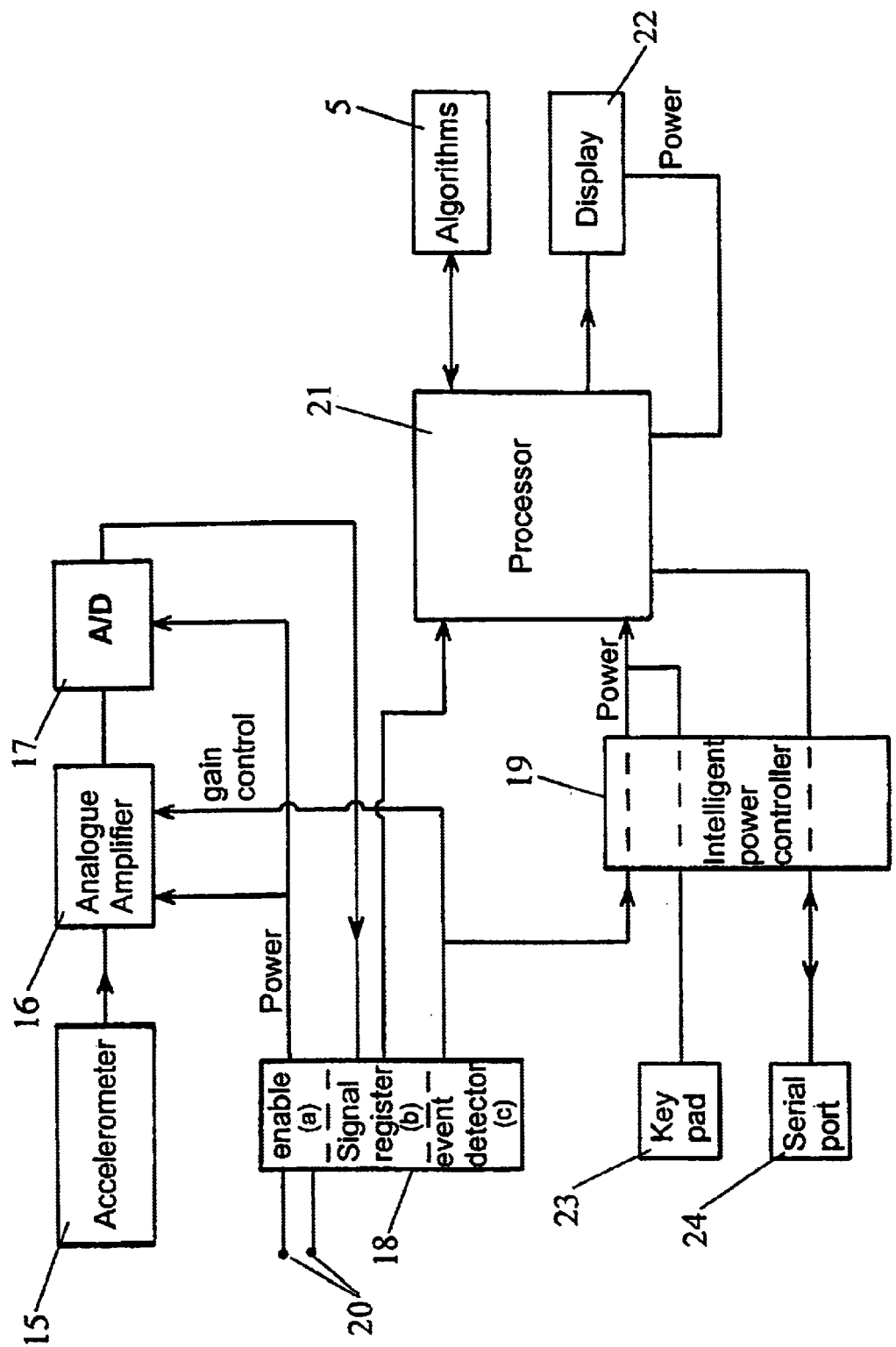
FIG. 6 is a block diagram of the preferred electronic hardware.

A block diagram of the electronic hardware is drawn in FIG. 6. The accelerometer 15 is coupled to an analogue amplifier 16 which incorporates a gain control function. The state of the entire instrument is controlled by two programmable logic devices numbered 18 (the event controller) and 19 (the intelligent power controller). When powered up, only parts of these PLDs are operative, and since they are not switching, standing current is very low. When the enable switch 20 is closed the PLD 18 turns on the Analogue section 16 and the A/D converter 17, and digitised samples from the accelerometer are fed to the signal register (b) in the PLD. If the signal exceeds a threshold, the event detector (C) of PLD 18 assumes that the log or sample has been struck. The event starts the logarithmic increase in the analogue amplifier gain, and inititiates the Intelligent power controller PLD 19 which powers up the microprocessor 21.

The microprocessor 21 records a number of digitised values over an ensuing time. Typically, 2048 readings will be taken over 400 ms, following which the analogue amplifier and A/D converter are turned off. The data are then Fourier transformed following appropriate windowing and filtering. The particular data record described combination will yield a maximum frequency of 2.5 kHz with a resolution of 2.5 Hz, which suits forest applications, but could be changed to suit other needs.

The power spectrum is then analysed by the processor 21 using algorithms discussed in the next section to extract a fundamental resonance $f_0$, and an answer displayed in the liquid crystal unit 22. This can consist of a single value for velocity, (assuming a prior log length has been entered into the unit), using the formula $$V=2f_0L$$

where L is the length, or the value can be converted to a speed class, and the code for that class displayed, for example "green" to indicate a colour marker to be used.

Having initiated the display, the microprocessor returns to hibernation mode to save current, and reactivates after a time of for example 30s to turn the display off under the control of the intelligent power controller 19.

It is necessary to manually enter some information, for example new log lengths. Operation of the key pad 23 is detected by the power controller PLD 19, which activates the processor 21 long enough to store the new data.

The unit is configured to deliver the minimum necessary information to operating crews, but clearly the full detail of spectral information, which may be required for R and D operations, is potentially available. The logic of the controller 19 is configured so that by keyboard entries, it is possible to send the spectral information via serial port 24 to an external computer for graphical display or data recording. Conversely, data received at the serial port activates the power controller and thence the processor, so that the serial port can be used to control the operation of the device from an external computer.

Spectrum Interpretation

It is well known that exciting a beam or log of wood into longitudinal oscillation produces a disturbance which can be Fourier analysed into a series which is harmonic, and in which the speed of sound in the wood is given by $$V=2Lf_0$$

V is the speed of longitudinal compressional motions along the member, and since the lateral boundaries are stress free, is given by the well known relation $$V^2=E/\rho$$

where E is Young's modulus, and $\rho$ the material density.

In samples of regular cross section, particularly where these are slender, higher resonances are closely harmonically related to the fundamental. Extraction of the modulus using the two equations above is simple since the fundamental is easily identified. The number of harmonics detected depends on the frequency characteristics of the exciting impulse. Wet wood is soft. Typically a hammer is arrested in a time of the order of a millisecond and the spectra cannot be expected to contain harmonics greatly in excess of the inverse of this time, i.e., greatly above 1 kHz. However, modeling studies we have made show that slenderness of the beam is a factor also. Thin beams or logs encourage the excitation of high harmonics, while short fat beams or logs do not.

In practice, there is a variety of circumstances where this picture requires modification to extract reliable values of the modulus.

In field use, samples may not be slender—a four meter saw log with a diameter of 50 cm is a considerably "fatter" than a sawn beam 100 by 50 mm, and because of the excitation spectrum and the log shape, few harmonics will be detected in the log compared with the sawn wood. A decision on which frequency should be identified as the fundamental may be less clear for the log. We have found that this can be exacerbated by the presence of unwanted noise spikes in the spectrum, or unwanted resonances arising from less than optimum hammer blows. Situations of poor spectra have been found to be inevitable in some physical locations, for example when obtaining spectra from the logs of cross-cut stems, when the log faces are relatively inaccessible. In development work, it is possible to repeatedly take a spectrum until by chance it is "clean". In a production tool, a high success rate in analysis must be available, and a built-in indication of the confidence in the answer is desirable.

It is also recorded in the literature that spectra from logs in stacks may differ from harmonic. We have observed that the fundamental can be typically 5% higher than the value expected from the resonance identified as the second harmonic, and values of 10% have been seen. Calculating MOE based on the fundamental or the second harmonic in this case would have a discrepancy of 20%, which is unacceptable.

Tests done on logs measured first in a stack and then unstacked on bearers show that it is the fundamental which is shifted most. The second harmonic is affected by about 1% by stacking effects, and higher harmonics, where seen, are approximately unchanged. As a rough guide, the second harmonic is a more reliable estimate of stiffness and/or strength than the fundamental. Always, any frequency shift of the fundamental is positive.

However, some short logs, measured in isolation on bearers, still show a small but measurable departure from a harmonic series, usually with the higher harmonics at frequencies below what would be expected.

In the case of stems, the departure can be enormous. Since stems are "slender" many harmonics can be excited in the region below 1000 Hz, and the lowest member of the series, if the fundamental, has been observed to be as much as 40% above the value implied by the higher harmonics. This would lead to a difference of two in the predicted value of stiffness and/or strength.

All the foregoing situations must be allowed for in the analysis software.

Finite Element modeling of the eigenmodes of the logs and stems has been carried out to gain an understanding of the factors involved in departures from harmonic series.

The results show that for a cylindrical log, the lowest resonance frequencies are closely harmonic. This remains true when the anisotropic elasticity of wood is included. The frequency of the fundamental mode is only slightly affected by the value chosen for Poisson's Ratio, which is fortunate since this parameter is ill-defined in wood. Further, no evidence was found that radial structure in logs, approximated by an inner core of low stiffness and/or strength surrounded by a stiffer outer cylinder produced other than some average spectrum of the two; i.e. such internal structure is not responsible for unharmonic effects.

At a frequency when the wavelength across the log approaches the wood diameter, the longitudinal frequencies become lower than expected i.e. a harmonic pull-down of the kind described earlier is seen. Due to the fact that the sound speed across the log is of the order of one tenth the longitudinal speed, this condition may be reached at what may be surprisingly low harmonic numbers in "fat" logs. Model results showed that ill-defined body resonances prevailed at higher frequencies. In other words, the spectra of short fat logs might be expected to show a small lowering of higher harmonics compared to the fundamental, but few harmonics will be seen. This roughly accords with our observational experience. The theory shows that for non-tapering logs, not stacked, the best indication of stiffness and/or strength comes from the fundamental.

The situation for stems is different because of their taper. Taper is the only parameter found which causes the resonances following the fundamental to be sharply lowered in frequency. However, the modeling shows that it is the low harmonics which are raised above the value expected from the wood modulus, while the high harmonics still indicate stem stiffness and/or strength. As with non-tapered logs, when the transverse wavelength of a resonance frequency approaches the stem diameter, the harmonic frequency tends to fall lower than expected. Because for stems, the frequency at which this is predicted to occur is high, the effect is unlikely to be seen and indeed we have not observed it.

Tapered-log modeling shows that it is the taper per wavelength which is important. The imbalance or asymmetry occurring in the oscillating mass and spring forces about each node in the log is the underlying cause of frequency shift. Thus the fundamental mode, where the stem is half a wavelength long, can be strongly affected. The taper per wavelength in the $N^{th}$ harmonic is only $1/N$ of that in the fundamental. The higher harmonics are much less affected by the taper and yield the correct stiffness and/or strength. Modeling shows, and our experience confirms, that to a reasonable approximation, if the fundamental resonance frequency is raised by a factor $ke^{-1}$ over its value expected on the basis of the stem length and stiffness and/or strength, the $N^{th}$ harmonic will be raised by a factor $ke^{-N}$ over its harmonic value. Resonances therefore fairly quickly reach their harmonic values.

We believe that the cause of the rise in the fundamental resonance of stacked logs noted earlier also lies in asymmetry similar to the case of the tapered stem. Now, the effect is that a log may be pinned to its neighbour in only two or three places. For low harmonics, this can produce a major elastic asymmetry and consequent lifting of the fundamental. Most of the nodal sections of the higher harmonics will not see the pinning points and their frequencies will be little affected.

Figure 2:
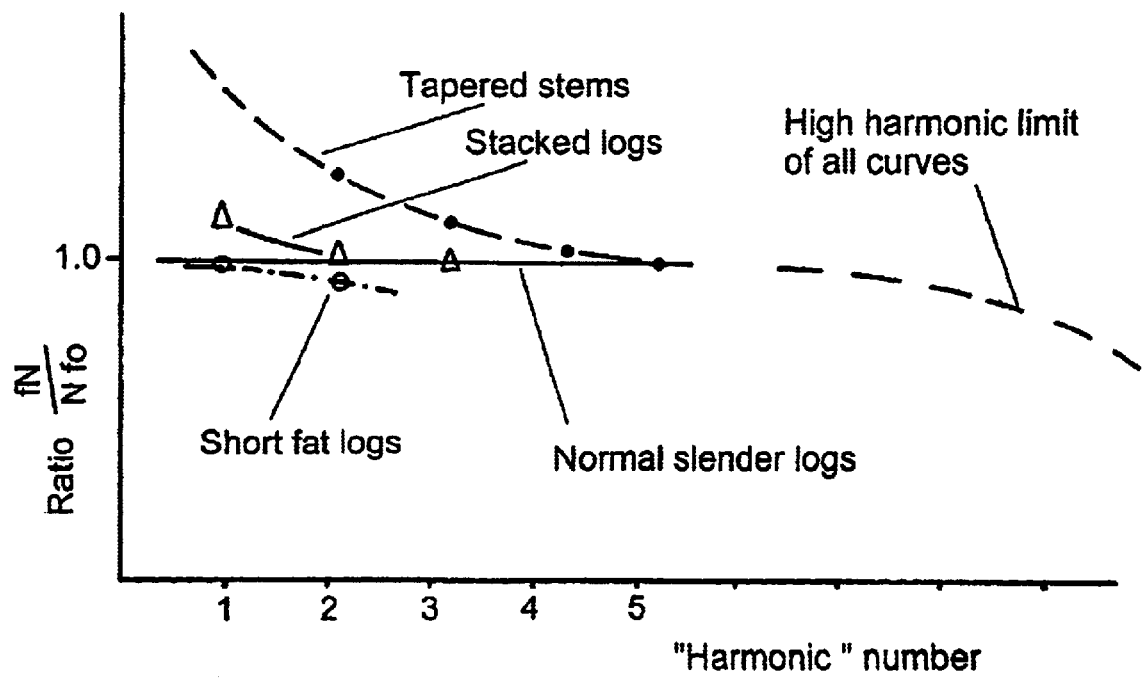
FIG. 2 illustrates schematically the types of spectra derived from long and short stems plotted as fn/Nfo against harmonic number.

The various cases described are illustrated in FIG. 2, where $f_N$ is the frequency of the $N^{th}$ member of the harmonic series sought, and $f_0$ is the "true" fundamental, or lowest member of the series, from which the velocity and stiffness and/or strength can be found. The lowest member $f_1$ coincides with $f_0$ if the log is slender and non-tapered.

This background of observation and modeling results provides the basis of the algorithms used to analyse stem spectra. While a velocity can be judged by an operator from a screen display of spectra, an automatic system needs to allow for noise peaks, non harmonic effects, and perhaps most confusing to an automatic process, missing spectral peaks which confuse the identification of a series.

The algorithm must reject occasional noise peaks in the spectrum, which means that as many as possible of the resonant peaks should be identified, since random noise spikes will not occur in harmonic ratios. It must allow for the fact that frequencies may be non-harmonic to a small extent in short logs and greatly so in stems and it should not require all members of a series to be present.

The identification system first considers only spectral signals above a threshold, for example those within 20% of the power of the largest spectral peak. It may be advantageous to smooth data in the frequency domain before doing this if signals are noisy to limit the number of peaks to be considered.

Given the length of a log and a likely range of sound speed, the possible range of frequencies for a fundamental is calculated and spectral peaks sought within that range. The search is done within velocity windows whose ranges are less than 2:1. Within such a window, the range of possible fundamental frequencies cannot overlap the consequent second harmonic range, and so allows fundamental and second harmonic to be distinguished. If no successful identification is ultimately made within this window, subsequent searches are made within modified velocity windows. This is generally not required. Most green *p. radiata* logs have velocities between 2.5 and 4 km/s which fulfills the velocity criterion.

For each potential candidate for a fundamental resonance, a filter comb is constructed. For example, if the peak to be tested had a frequency of 300 Hz, a comb consisting of 300, 600, 900, Hz is constructed, and the energy measured within that comb by adding the power at the comb frequencies. For short logs, a deviation of a few percent is allowed, i.e., energy is considered to be part of the comb if it falls within a predetermined band about the expected centre, to take account of the effects described earlier which are encountered in practice.

A useful variation of this procedure, which takes into account the stacking effect, is to base the comb search on the second harmonic, since this is relatively little affected by stacking, and to allow deviations from harmonic to fall mainly at the fundamental frequency. The velocity, and modulus, are then calculated from the second harmonic by assuming that this is the frequency $2f_0$.

This procedure is repeated for all peaks which are candidates for the fundamental within its allowed frequency range. The preferred identification is that spectral peak whose comb accounts for the greatest quantity of spectrum power. A numerical confidence measure which follows from this procedure is the ratio of the power accounted for in the peaks within the comb to the sum of power in other peaks plus the background noise level.

In the search to identify harmonic members, no power considered in peaks which fall at frequencies which would lead to impossibly low velocities. The reason for this is that such peaks can be generated by moving the accelerometer head during the course of recording data. Nevertheless, their inclusion in the confidence measure gives operator warning that such an event might have happened.

It will be occasionally found, particularly with short "fat" logs, that only one resonance is seen. In that case, provided it produces a plausible velocity, it must be assumed to be the fundamental.

The procedure is modified for stems where taper is important resulting in a grossly non-harmonic series. A range of fundamental frequencies is sought as before, but the comb generated is considerably modified. Because the procedure is more complex and suits the presence of many harmonics, it is only applied to logs above a preset length, for example 12 m.

If $f_0$ is as before the "true" fundamental from which the speed in the tapered log can be found and the modulus calculated, the exponential deviation from a harmonic series described earlier can be expressed as $$(f_N - Nf_0)/f_N = ke^{-N}$$

Here $f_N$ is the frequency of the $N^{th}$ harmonic, and k is a constant between 0 and 1, which must be determined. Having identified one peak as a possible fundamental (i.e. N=1), for a given value of k, a value of $f_0$ is defined, and a comb of frequencies can then be generated at which the other harmonics should fall. The power falling within the comb is summed as before, and the procedure repeated with different values of k to find the optimum match for that presumed fundamental mode.

This procedure will sometimes yield two values of k which generate equal summed powers. A second measure is therefore taken at each value of k to express how closely the comb is fitted. This is the sum of the deviations of each peak from its comb centre frequency. The choice is made on the basis of the most power and the best comb fit.

The next candidate resonance for the fundamental is then tested, and classed as a better identification or not on the basis of both the resonance power accounted for, and the closeness of fit to the comb. With a fast processor, computation time is acceptably short.

In effect, a transformation is being done to best fit the given resonances to a harmonic set, and does not require all member of a series to be present. It could begin by generating a comb by assuming that a particular peak was the $N^{th}$ harmonic and generating a comb from that. In fact, the algorithm does this, testing each peak in turn to be a particular harmonic of an assumed series, and finding the goodness-of-fit for each combination. This is useful since some stem signatures have an ill-defined fundamental frequency.

The complexity of the these procedures is frequently not needed because many resonance spectra have an obvious interpretation. Their need is in the general case, when a reliable answer is needed in a high percentage of cases from less than perfect data, and the data itself must be used to indicate to unskilled operators whether or not the answer is reliable.

What is claimed is:

1. A method of log making from a stem of a felled tree of a species having a predictable variation in stiffness characteristics along its length with a view to maximizing stiffness extracted value whilst the tree is still in a sufficiently green felled condition that a sap contribution dominates its density to an extent that should longitudinal acoustic waves be generated therein a measure of average stem acoustic speed V for the tree stem can be derived such that (a) $V^2$ will correlate with an average modulus of elasticity (MOE) for the tree stem, and (b) $V^2$ is considered a measure of an average MOE for the tree stem on a basis of an assumption that the density of the greenwood is constant for the species and that a water loaded density for the species is an appropriate density for the $V^2$ to MOE relationship MOE density x $V^2$, said method comprising the steps of (i) inducing from an end of the tree stem a disturbance which travels an entire length of the stem, repeatedly reflecting at ends thereof, and in so doing generating a series of acoustic waves with a frequency spectrum, and collecting at least part of the frequency spectrum, (ii) deriving at least a function of V or at least a function of $V^2$ reliant upon a measurement of a transit time of the waves along the stem length L, (iii) by reference to predictable variations in speed along the length of a tree stem of that species having V, function of V, $V^2$ or function of $V^2$, estimating via one of predicted position-dependent speed, average MOE and another stiffness characteristic for several logs to be cut using viable cut options from the tree stem, and (iv) making the cut decisions reliant on the one of predicted position-dependent speed, average MOE and another stiffness characteristic for each of several logs by reference to values for the logs of estimated individual stiffnesses.

2. The method of claim 1, wherein step (i) involves, at a same end of the tree stem, both striking of the end of the tree stern and detecting of at least part of the spectrum of resonant plane acoustic waves created in the tree stem as a consequence.

3. The method of claim 2, wherein the step (ii) measure of transit time is by a derived fundamental frequency $f_0$ of the at least part collected acoustic spectrum.

4. The method of claim 3, wherein $f_0$ is derived by a best fit spectral analysis of the resonant frequencies in the acoustic spectrum as collected.

5. The method of claim 4, wherein one of V and $V^2$ is derived from $f_0$ using the relationship $V = 2 f_0 L$.

6. The method of claim 1, wherein the speed V is measured by reference to echo time T of the wave along a stem of length L.

7. The method of claim 1, wherein step (i) is wholly performed at one end of the tree stem.

* * * * *